(12) United States Patent
Downie (10) Patent No.: US 8,336,544 B2
(45) Date of Patent: *Dec. 25, 2012

(54) VOLUME FLOW CONTROLLER

(75) Inventor: Neil Alexander Downie, Odiham (GB)

(73) Assignee: Air Products and Chemicals, Inc., Allentown, PA (US)

(*) Notice: Subject to any disclaimer, the term of this patent is extended or adjusted under 35 U.S.C. 154(b) by 357 days.

This patent is subject to a terminal disclaimer.

(21) Appl. No.: 12/537,608

(22) Filed: Aug. 7, 2009

(65) Prior Publication Data

US 2010/0180892 A1    Jul. 22, 2010

Related U.S. Application Data

(62) Division of application No. 10/534,781, filed as application No. PCT/GB03/05064 on Nov. 20, 2003, now Pat. No. 7,669,594.

(30) Foreign Application Priority Data

Nov. 20, 2002   (GB) .................................. 0227109.6

(51) Int. Cl.
*A61M 11/00*    (2006.01)
(52) U.S. Cl. ................................. 128/203.12
(58) Field of Classification Search ............ 128/203.12, 128/203.14, 200.24, 204.21–204.23
See application file for complete search history.

(56) References Cited

U.S. PATENT DOCUMENTS

| | | |
|---|---|---|
| 3,774,395 A | 11/1973 | Greune et al. |
| 3,893,291 A | 7/1975 | Davis et al. |
| 4,125,123 A | 11/1978 | Clingman, Jr. |
| 4,681,530 A | 7/1987 | Huber |
| 5,307,668 A | 5/1994 | Vander Heyden |
| 5,331,995 A | 7/1994 | Westfall et al. |

(Continued)

FOREIGN PATENT DOCUMENTS

EP    0661071 A1    7/1995

(Continued)

OTHER PUBLICATIONS

Downie, Neil; Industrial Gases; published by Blackie Academic publishers (an imprint of Chapman & Hall), 1997, ISBN 0751403520; p. 147-159.

*Primary Examiner* — Steven Douglas
(74) *Attorney, Agent, or Firm* — Willard Jones, II (57) ABSTRACT

A volume flow controller (1) for controlling the flow of a gas mixture of variable proportions through a conduit (3) has a valve means (5) for regulating the flow of gas through the conduit, a drive means (9) for driving the valve means, a volumetric flow meter (7), such as a Pelton wheel, for measuring the flow of gas through the conduit, which provides a feedback signal (29) for comparison with a setpoint signal (17) in an amplifier (15) which generates an adjustment signal (11) which is fed to the drive means. The setpoint signal is generated by a setpoint signal generating means (19), which comprises a potentiometer (21) for inputting a value corresponding to a desired flow rate and a slowdown circuit (23) consisting of a resistor (25) and a capacitor (27) for delaying the change in the setpoint from the previous setpoint to the desired setpoint for a period of time sufficient to compensate for the delay in response inherent in the volumetric flow meter, thus providing smooth and stable control of the gas flow. Preferably, the potentiometer is a digital potentiometer (403), which voltage is variable by independent manipulation of rotary encoders (417).

9 Claims, 5 Drawing Sheets

U.S. PATENT DOCUMENTS

| | | | |
|---|---|---|---|
| 5,727,545 | A | 3/1998 | Psaros |
| 5,865,205 | A | 2/1999 | Wilmer |
| 5,975,126 | A | 11/1999 | Bump et al. |
| 6,236,041 | B1 | 5/2001 | Donnerhack et al. |
| 7,434,580 | B2 | 10/2008 | Downie et al. |
| 2002/0148471 | A1 | 10/2002 | Hirabayashi |

FOREIGN PATENT DOCUMENTS

| | | |
|---|---|---|
| EP | 0834723 | 8/1998 |
| JP | 61-133414 A | 6/1986 |
| JP | 02-099831 | 4/1990 |
| JP | 02-277539 A | 11/1990 |
| JP | 04-262408 | 9/1992 |
| JP | 07-155380 A | 6/1995 |
| JP | 7-209044 A | 8/1995 |
| JP | 08-038605 | 2/1996 |
| JP | 08-304134 A | 11/1996 |
| JP | 10-227670 A | 8/1998 |
| JP | 11-065673 | 3/1999 |
| JP | 11-161342 A | 6/1999 |
| JP | 2000-501956 | 2/2000 |
| JP | 2000-501956 A | 2/2000 |
| JP | 2002-116076 | 4/2002 |
| JP | 2002-136596 | 5/2002 |

VOLUME FLOW CONTROLLER

CROSS-REFERENCE TO RELATED APPLICATIONS

This application is a divisional application of U.S. application Ser. No. 10/534,781, filed Nov. 18, 2005, which is the national stage entry of PCT/GB03/05064, filed Nov. 20, 2003, which claims priority to United Kingdom application No. 0227109.6, filed Nov. 20, 2002.

DESCRIPTION OF THE INVENTION

The present invention relates to apparatus for controlling the flow of a gas, apparatus for providing a gaseous mixture to a medical device, apparatus for controlling the rate of flow of gas through a conduit and a method of controlling the flow of a gas mixture of variable proportions.

In the embodiments, the present invention relates generally to methods and apparatus for controlling the flow of a gas mixture having varying proportions of gaseous components.

Apparatus and methods for controlling the flow of fluids and, in particular, feedback mechanisms for flow regulating means are known.

Electronic mass flow controllers (MFCs) are well known for use in controlling the flow of gases and liquids. A mass flow controller typically consists of a thermal mass flow meter (MFM) downstream of a solenoid flow regulating valve. The mass flow meter typically consists of two heating coils, one downstream from the other, which are heated and the measurement corresponds to the heat passed by the first coil to the gas as detected by the second coil. Whilst providing an almost instantaneous response, it depends upon the specific heat capacity of the gas being metered and can be calibrated for the gas of interest (or calculated, e.g. with a microprocessor, if calibrated for a different gas than the gas of interest). The MFM does not, therefore, accurately measure the volume in gas mixtures where there is variation in specific heat capacities and other properties of the components, e.g. in mixtures with Xe and $O_2$.

U.S. Pat. No. 4,681,530 discloses a device for the supply of fuel gas and oxidizing agents to the burner of an atomic absorption spectrometer. Fuel gas, e.g. acetylene, and an oxidizing agent, e.g. $N_2O$ or air, are provided to an atomic absorption spectrometer burner via pressure regulators which are adjusted by servo motors then through restrictors and finally through flow meters. The flow meters are connected to a control unit, which may be a microprocessor, to provide the control unit with a measure of the rate of flow of the fuel gas and the oxidizing agent. The control unit sends a signal to the servomotors for adjustment of the pressure regulators. Flow meters of the form of a turbine wheel rotatably mounted in a housing, co-operating with a signal generating means for generating output signal as a function of angular rate of the turbine wheel are described.

The flow controller described in U.S. Pat. No. 4,681,530 includes a true volume flow meter providing an accurate measure of the gas flow regardless of the components' physical properties. In low volume, small-scale systems, this is likely to provide an almost instantaneous measurement although there is likely to be at least some delay. However, when the scale is increased and a larger volume of gas flow is required to be controlled, the delay may become significant. Furthermore, in those situations where the gas is required with precise accuracy for a medical device, microprocessors requiring programmable software applications to account for delays is undesirable.

U.S. Pat. No. 3,774,395 describes an electrical fuel control system for a gas turbine engine in which the inlet of fuel into a turbine burner is determined by comparison of the desired acceleration, which may be represented by a desired gas turbine temperature, with the actual temperature as measured by a thermocouple situated in the turbine. Due to the time lag in the response of the thermocouples, a compensation circuit is provided. However, the compensation circuit is provided to the feedback signal from the thermocouple and is complicated by the inclusion of other factors, such as the engine inlet temperature and the gas generator speed in order to provide a predicted thermocouple temperature for comparison with the desired temperature. The compensation circuit includes RC circuits where a potentiometer is in parallel with two capacitors and in series with 4 resistors, all of which are variable and which may be set to represent time constants associated with the thermocouple. The circuit can incorporate other factors associated with the operation of the engine. U.S. Pat. No. 3,893,291 describes a similar system which further incorporates a safety factor into the feedback signal, which feature consists of a maximum turbine temperature corresponding to safe operation of the turbine having regard for predicted air flow caused by the desired acceleration.

EP-A-0661071 describes a device for providing continuous positive airway pressure breathing (CPAP) in the treatment of sleep apnea, which device automatically starts and/or stops depending upon whether the patient is wearing a mask. A mask has a wearing detection means which is provided either by the completion of a circuit or by the induction of a current by contact of the mask with the patient's face or by the detection of a pressure in the apparatus greater than a threshold pressure. A signal is then generated to switch on a flow generator (turbine), driven by a motor speed controller. The speed of the turbine depends upon a preset mask pressure required for the CPAP treatment. The turbine is switched off on removal of the mask, which can be detected by the motor speed increasing to a threshold value in response to failure of the turbine to generate the preset mask pressure, by comparison of a voltage generated by the motor with a threshold value. To prevent the turbine being switched off due to transient or intermittent reductions in mask pressure below the predetermined threshold, a resistor-capacitor circuit (RC circuit) is introduced prior to the comparison of the motor speed generated voltage with the predetermined threshold. The RC circuit provides a timer which delays the full signal from the motor reaching the comparator unless it is maintained for a preset time period, which time period is inherent in the values of the resistance and capacitance of the resistor and the capacitor respectively.

It is desirable to provide a volumetric feedback system by which the flow of gases of varying specific heat capacities may be accurately measured and accurately controlled.

Accordingly, in a first aspect of the invention, there is provided an apparatus for controlling the flow of a gas mixture of variable proportions comprising a conduit for the flow of gas, a delivery means for delivery to the conduit of a gas mixture having gaseous components in controlled variable proportions, a valve means for regulating the flow of gas through the conduit, a drive means for operating the valve, a setpoint signal generating means for generating a setpoint signal according to a desired setpoint, a volumetric flow meter situated downstream of the valve, a feedback signal generating means associated with the volumetric flow meter, said feedback signal corresponding to the flow rate measured by the volumetric flow meter, and an adjustment signal generating means for generating an adjustment signal for controlling the drive means by which the valve means is operated to open or close by an amount corresponding to the adjustment signal to achieve a desired flow rate corresponding to the desired setpoint, which adjustment signal generating means comprises a comparing means for comparing the setpoint signal and the feedback signal. The apparatus of the present invention is conveniently termed a volume flow controller.

In a second aspect of the invention, there is provided an apparatus for correcting the flow of gas through a conduit, which flow is regulated by a valve means operated by a drive means in response to a setpoint signal generated, from a desired setpoint corresponding to a desired gas flow rate, by a setpoint signal generating means which is connected to said drive means, said apparatus comprising a volumetric flow meter for measuring the rate of flow of gas through the conduit downstream of the valve means, a feedback signal generating means associated with the volumetric flow meter, said feedback signal generating means for generating a feedback signal corresponding to the flow rate measured by the volumetric flow meter, and a comparing means for generating an adjustment signal for correcting the rate of flow, wherein the setpoint signal generating means is connected to the drive means via the comparing means in which the setpoint signal is compared with the feedback signal and the setpoint is corrected by reference to the feedback signal to produce an adjustment signal for transmission to the driving means to adjust the valve means to cause a change in the rate of flow of gas therethrough thereby reducing any discrepancy between the desired gas flow rate and the measured gas flow rate.

Preferably, the setpoint signal generating means is connected to the drive means via the comparing means, without any connection via a microprocessor and may, for example, be hard-wired.

The term "hard-wired" includes connections involving or achieved by permanently connected circuits designed to perform a specific function and preferably do not include programmable circuits.

These aspects of the present invention are particularly advantageous for controlling the flow of a gas composition comprising at least two gaseous components of varying proportions, which two gaseous components have different molar specific heat capacities at constant pressure, $C_p$ (J K$^{-1}$ mol$^{-1}$). The flow meter used in a mass flow controller (MFC), a mass flow meter (MFM), measures the thermal mass flow rate ($V_T$/lmin$^{-1}$) of the gas. This value is related to the volumetric flow ($V_{dot}$/lmin$^{-1}$) of the gas by the following equation:

$$V_T \alpha V_{dot} C_p$$

The flow rate as measured by a thermal mass flow meter is therefore proportional to the molar specific heat capacity of the gas at constant pressure. In many instances this is unlikely to cause a significant problem in measuring the flow rate because, many common gases have similar molar specific heat capacities. For example, hydrogen, nitrogen and oxygen all have quite similar molar specific heat capacities, and thus the error in measurement of the volume of each of those gases or a mixture of those gases using an mass flow meter (without recalibrating) is relatively small. The molar $C_p$-values of some common gases are shown in Table 1.

TABLE 1 molar specific heat capacities, $C_P$ of some common gases

| Gas: | He | Ar | Xe | $H_2$ | $N_2$ | $O_2$ | $CO_2$ | $NH_3$ | $CH_4$ | $SF_6$ |
|---|---|---|---|---|---|---|---|---|---|---|
| $C_P$: | 21.5 | 20.8 | 20.8 | 28.7 | 29.0 | 29.0 | 36.0 | 35.5 | 35.4 | 95.2 |

However, when the gas composition comprises at least two gaseous components having different molar $C_p$-values, a mass flow meter calibrated for one of the gases will give a significantly different measurement of volume when measuring the mixture or the other component.

The apparatus of an example of an embodiment of the present invention, however, will provide an accurate measurement of the rate of flow of the gas composition independent of the molar $C_p$-values of each of the components of the composition.

Preferably, the apparatus further comprises a gaseous composition, the rate of flow of which is to be controlled. The gaseous composition preferably comprises xenon in admixture with oxygen and/or nitrogen. Further gases may be included in the composition if desired.

The volumetric flow meter may be any means of measuring the true volume flow through the conduit and is preferably of the turbine wheel type of flow meter, such as, for example, a Pelton wheel flow meter.

The feedback signal generating means is preferably provided for co-operation with the flow meter, such as a turbine wheel flow meter, and preferably comprises a means of determining the angular rate of the turbine wheel, e.g. by way of an LED/photodiode assembly or a magnet/Hall-effect switch activated by the rotor giving a pulse rate proportional to the flow rate, and a frequency-to-voltage converter circuit which provides a feedback signal as its output. This feedback signal corresponds to the measured flow rate through the conduit. Alternatively, the feedback signal comprises an integral component generated by way of an integrator situated after the output of the volumetric flow meter.

Optionally, the feedback signal generating means may be such that the feedback signal comprises a proportional component and a time differential (dV/dt) component or an integral component and a time differential component of the volumetric flow rate. As a further option, the feedback signal may have a proportional component, a time differential component and an integral component and the feedback signal generating means may therefore incorporate a Proportional, Integral, Differential (PID) device.

Contrary to normal operation, in the present invention, the optional PID device is preferably situated at the volumetric flow meter output, rather than after the output of the comparing means.

As a further alternative, an integrator, for integrating the difference between the setpoint signal and the feedback signal can be placed in the circuit after the comparing means.

However, a feedback signal in which there is at least a proportional component is preferred.

The setpoint signal generating means preferably comprises a means for inputting a desired setpoint, which corresponds to the desired flow rate, and preferably the means for inputting the desired setpoint is a potentiometer.

The setpoint signal generating means generates a setpoint signal which may be compared with the feedback signal in the comparing means. The comparing means may be a digital comparator or preferably is an operational amplifier or a differential amplifier.

Preferably the comparing means is a differential amplifier, which preferably has a programming resistor to increase the gain of the amplifier, for example, by 20 times, so that even small discrepancies between measured flow rate and the desired flow rate can be corrected.

When the feedback signal consists of an integral component rather than a proportional component, a proportional amplifier is preferred.

However, in a preferred embodiment of the invention where the volumetric flow meter is a turbine wheel flow meter, there is an inherent delay in the response of the flow meter to changes in the rate of flow through the conduit. It may be, for example, up to 10 seconds before the measured flow rate accurately reflects the actual flow rate through the conduit. The length of the delay in response is dependent on a number of factors, including the relative cross-sectional area of the flow meter inlet as compared to the cross-sectional area of the conduit, the rate of flow through the conduit and the magnitude of the change in flow rate effected, as well as the physical condition and/or properties of the flow meter. If the setpoint signal generated by the setpoint signal generating means is an instantaneous reflection of the desired setpoint input into the potentiometer, the initial difference between the setpoint signal and the feedback signal will be proportional to the difference between the desired setpoint and the previous setpoint and the adjustment signal will reflect this causing the valve to open or close sufficiently to provide a flow corresponding to the new desired flow rate. After, say, 1 second, the delay in response of the flow meter results in a feedback signal unrepresentative of the actual flow rate through the conduit, and the comparing means will compare the setpoint signal with the feedback signal and result in an adjustment signal which does not accurately reflect the difference between the desired flow rate and the actual flow rate and will cause the valve means to open or close even further, significantly shifting the flow rate from the desired flow rate. Depending upon the speed of response of the flow meter and the rate of flow through the conduit, this will either result in an unstable system where the valves moves cyclically from fully opened to fully closed, or will eventually provide the desired flow rate by a delayed iterative mechanism.

The provision of a "slowdown" circuit as part of the setpoint signal generating means is a preferred feature of the present invention and causes the setpoint signal to increase or decrease over time until the setpoint signal corresponding with the desired setpoint is reached.

In a preferred embodiment of the invention, the slowdown circuit comprises an RC-type circuit, such as one with a resistor in series with a potentiometer (upon which the desired setpoint may be set) and a capacitor to earth in parallel with the potentiometer. This is capable of providing a time over which the setpoint signal may be increased or decreased to compensate for the delay in response of the volumetric flow meter and gives a surprisingly accurate and stable performance. The actual period of time over which the setpoint signal is increased or decreased, the magnitude of which increase or decrease corresponds to the difference between the previous setpoint and the desired setpoint, is a function of the resistance of the resistor, the capacitance of the capacitor and the voltage applied across the capacitor. The voltage applied across the capacitor is the difference between the previous setpoint voltage on the potentiometer and the desired setpoint voltage on the potentiometer, each of which corresponds to a flow rate through the conduit. The time period (t) over which the setpoint signal is increased or decreased until a setpoint signal corresponding to the desired setpoint is reached may be expressed by the following formula:

$$\Delta V = \Delta V_0 e^{(-t/RC)}$$

where $\Delta V$ is the difference between the desired setpoint and the actual setpoint, in volts (V), at any particular time, t (s), $\Delta V_0$ is the initial difference between the desired setpoint and the previous setpoint (i.e. at time t=0), R is the resistance of the resistor, in kilo-ohms (k$\Omega$), and C is the capacitance of the capacitor, in microFarads ($\mu$F).

Preferably, for the control of gas flow, at a rate of from 0 l/min to about 10 l/min through conduit for feeding gas to a medical device such as a cardiopulmonary bypass oxygenator or a ventilator, when a turbine wheel volumetric flow meter is used, the setpoint signal generating means, incorporating the slowdown circuit, comprises a potentiometer variable between 0 V and 5 V corresponding to a flow rate through the conduit of 0 l/min and 10 l/min, a resistor having a resistance of about 330 kO and a capacitor having a capacitance of about 40 $\mu$F.

An example of a suitable turbine wheel volumetric flow meter for use in accordance with the present invention is the Model 100 Flo-Sensor™, available from McMillan Company, but adapted by blocking the by-pass tube.

Optionally, a slowdown circuit having a reduced time component may be incorporated and the effect of the reduced delay may be offset by an enhanced feedback signal from the volumetric flow meter. For example, the feedback signal may consist of a proportional component, a time differential component and/or, optionally, an integral component.

Whilst, in the preferred embodiment of the present invention, a simple RC-circuit provides the delay in the slowdown circuit, more sophisticated filter circuits may be incorporated.

If a slowdown circuit is not incorporated into the setpoint signal generating means, alternative methods and apparatus for compensating for the delay in response of the volumetric flow meter may be used. For example, instead of hard-wiring the setpoint signal generating means to the drive means, via a comparing means, a microprocessor could be incorporated to provide delay compensation. However, in the provision of gases to a medical device, the use of a microprocessor, which requires software, is undesirable since defects in the software can occur which in the medical field may be critical. A hard-wired apparatus is of much greater reliability.

An alternative to employing a slowdown circuit as part of the setpoint signal generating means, whilst maintaining a hard-wired apparatus, is to compensate for any delay in response of the volumetric flow meter to changes in flow by providing the negative input of the comparing means with an enhanced feedback signal component. The enhanced feedback signal may be generated in response to a change in the signal on the potentiometer and may decay over time, which time corresponds to the response time of the volumetric flow meter. One method of creating such an enhanced feedback signal is by incorporating a suitable filter circuit connected directly between the potentiometer and the negative feedback input of the comparing means.

The valve means may be any device for regulating the flow of gas through a conduit. Preferably the valve means is a proportional solenoid valve.

The drive means may be any device or component which has the effect of powering the valve means to open or close by an amount represented by the signal provided to it. It may be a separate module or may be incorporated into the valve means. Preferably, the drive means is a driver module commonly used with proportional solenoid valves. The drive means preferably has an AC component in addition to a DC component, in order to prevent the valve sticking. The frequency of the AC component in the driver's output is preferably a high frequency, e.g. from 150 Hz to 400 Hz In a preferred embodiment, the volume flow controller of the present invention is incorporated into apparatus for providing and circulating a gaseous composition to a medical device, said apparatus comprising a main circuit for recirculatory flow of gas to and from said medical device, a gas source for providing gas to the main circuit; and the volume flow controller located to control the flow of gas to the medical device and/or from the gas source to the main circuit.

Preferably, the gaseous composition comprises a first gas and a second gas, the main circuit comprises a circulation pump for pumping gas through the circuit to supply the medical device with the gaseous composition, a gas outlet for connection to the medical device to supply gas thereto, a gas inlet for connection to the medical device to receive spent gas therefrom, a first supply conduit for supply of gas of a first composition from a first gas source to the circuit, a second supply conduit for supply of gas of a second composition different from said first composition from a second gas source to the circuit, a first supply flow controller i.e. control means for controlling the flow of gas through the first supply conduit, and a second supply flow controller i.e. control means for controlling the flow of gas through the second supply conduit and which apparatus further comprises a concentration determiner i.e. determining means for determining the concentration of at least one gas in the gaseous composition within the circuit and a means for venting gas from the circuit.

Preferably, the apparatus includes a bypass conduit, which permits at least a portion of the recirculating gas to bypass the gas outlet, the medical device and the gas inlet.

Preferably, the apparatus also comprises a gas outlet flow control means for controlling the flow of gas through the gas outlet to the medical device.

There is preferably provided a pressure maintaining means for maintaining the pressure to the gas outlet by controlling the flow of gas through the bypass conduit, for example, by use of a valve, whereby flow of gas through the bypass conduit is prevented unless a predetermined pressure, for example 30 millibar gauge (mbarg) (103 kPa absolute), is attained. The pressure will then be maintained upstream from the bypass conduit and thus also upstream from the gas outlet to the medical device at around the predetermined pressure, so that a setting on the gas outlet flow controller enables a constant flow of gas to the medical device.

In addition to, or instead of, the bypass flow control means, there may be provided a circuit volume regulating means for taking up temporary increases in recirculating gas volume and compensating for temporary decreases in recirculating gas volume. Preferably, said means is in the form of expansion bellows or the like. Preferably, there is also a monitor i.e. monitoring means for monitoring the degree of variation of the volume of recirculating gas. The monitoring means may be an ultrasonic or infra-red level sensor for detecting the level of the expansion bellows in an expandable direction thereof, but is preferably and ultrasonic level sensor.

The apparatus of the present embodiment preferably operates at a pressure of up to about 250 mbarg (125 kPa) through the bypass circuit, more preferably up to about 150 mbarg (115 kPa) and may provide gas to the medical device at a pressure of up to about 100 mbarg (110 kPa), but preferably about 30 mbarg (103 kPa). The circulation pump may circulate gas through the circuit at a rate of up to about 80 liters per minute (l/min), preferably up to about 30 l/min, more preferably from about 15 to about 20 l/imin and preferably supplies gas to the medical device at a rate of up to about 30 l/min, preferably up to about 10 l/min and still more preferably up to about 5 l/min.

Preferably, the gas outlet flow control means is a volume flow controller in accordance with an example of an embodiment of the present invention.

Each of the first and second supply flow control means may be, for example, a valve or a mass flow controller (MFC), but is preferably a volume flow controller of the present invention.

There may be one or more concentration determiners i.e. determining means and typically, the or each concentration determining means will be dedicated for analysis of a single component of the gas mixture. Preferably, the or each concentration determining means communicates with supply flow control means for controlling the supply of a respective gas, such that when the composition of the gas is found to exceed or fall below, as appropriate, a predetermined level or concentration, the supply flow control means is triggered to alter the flow rate of gas to the main circuit. For example, a minimum concentration of a first gas in the gaseous composition circulating through the apparatus may be desired and the analyser or other gas concentration determining means may be set by the operator to send a signal to trigger the relevant supply flow control means when the measured concentration falls below the desired concentration such that the flow of that gas into the circuit is increased, thereby increasing the concentration of that gas in circulation. Alternatively, the gas concentration determining means can provide a signal to alert the operator, for example, by way of an alarm, to the need to manually adjust the relevant supply flow control means.

The monitoring means for the circuit volume regulating means may communicate with the relevant supply flow control means, such that when, for example, the monitor indicates that the volume of gas in the circuit has fallen below a predetermined minimum level, a selected supply flow control means is triggered to alter the flow rate of gas to the main circuit to return the volume to the desired level. Depending upon which supply flow control means is selected and upon the composition of gas supplied through the selected supply conduit, the concentration of gases in the circuit may thereby be affected and/or controlled.

Communication of the concentration determining means or volume monitoring means with the supply flow control means may be via an analog electrical circuit, on which the gain may be set as desired. For example, for control of a supply of a gas which is rapidly consumed and/or urgently required by the medical device, the analog circuit may have a high gain. Conversely, for control of a supply of a relatively slowly consumed gas the analog circuit may have a low gain.

Preferably the medical device is a cardiopulmonary bypass oxygenator or an artificial ventilator. The apparatus is particularly applicable to use with a cardiopulmonary bypass oxygenator.

Alternatively, in another embodiment of the invention, the volume flow controller of the invention is incorporated into apparatus comprising a medical device requiring a supply of a gaseous composition comprising a first gas and a second gas, a main circuit for recirculating gas through the medical device and comprising a circulation pump for pumping gas through the main circuit, a gas outlet connected to the medical device, a gas inlet connected to the medical device, a first supply conduit for supply of gas of a first composition to the main circuit, a second supply conduit for supply of gas of a second composition different from said first composition to the main circuit, a gas outlet flow control means for controlling the flow of gas to the medical device, a first supply flow control means for controlling the flow of gas through the first supply conduit and a second supply flow control means for controlling the flow of gas through the second supply conduit, a concentration determining means for determining the concentration of at least one gas of the gaseous composition within the main circuit and a means for venting gas from the main circuit, wherein at least one of the gas outlet flow control means, the first supply flow control means and the second supply flow control means comprises a valve means, a setpoint signal generating means hardwired to said valve means and a volumetric feedback correction system.

Preferably, in accordance with the present embodiment, at least one of the gas outlet flow control means, the first supply flow control means and the second supply flow control means comprises a volume flow control means or flow control means in accordance with an example of an embodiment of the present invention.

In a third aspect of the invention, there is provided a method of controlling the flow of a gas mixture of variable proportions through a conduit having a valve means located therein against which is provided a known pressure of the gas mixture, said method comprising adjusting a setpoint on a potentiometer to a desired setpoint from a previous setpoint, which potentiometer is connected to a drive means for operating the valve means, said desired setpoint corresponding to a desired flow of gas through the conduit as controlled by the valve means, generating a setpoint signal from the adjusted desired setpoint on the potentiometer, measuring the rate of flow of fluid passing through the conduit using a volumetric flow meter downstream from the valve means, generating a feedback signal from the volumetric flow meter, comparing the feedback signal with the setpoint signal, generating an adjustment signal corresponding to the discrepancy between the setpoint signal and the feedback signal and adjusting the valve means, using the drive means, by an amount corresponding to the adjustment signal.

Preferably, the setpoint signal generating means is hardwired to the drive means and the feedback signal and the setpoint signal are compared using hard-wired electronics apparatus.

Preferably, the increase or decrease over time in the setpoint signal is provided automatically, for example by means of a slowdown circuit.

In a fourth aspect of the present invention, there is provided a method of providing a medical device with a gaseous composition comprising a first gas and a second gas in controlled variable proportions, said method comprising controlling the flow of a gaseous composition of a desired composition through a conduit leading to the medical device, said conduit having a valve means located therein which valve means, when closed is subject to a gas pressure of at least a desired level, by adjusting a setpoint on a potentiometer to a desired setpoint from a previous setpoint, which potentiometer is connected to a drive means for operating the valve means, said desired setpoint corresponding to a desired flow of gas through the conduit as controlled by the valve means, generating a setpoint signal from the adjusted desired setpoint on the potentiometer, measuring the rate of flow of gas passing through the conduit using a volumetric flow meter downstream from the valve means, generating a feedback signal from the volumetric flow meter, comparing the feedback signal with the setpoint signal, generating an adjustment signal corresponding to the discrepancy between the setpoint signal and the feedback signal and adjusting the valve means, using the drive means, by an amount corresponding to the adjustment signal, which method further comprises collecting spent gas mixture from the device, determining the concentration of each of the components of the gaseous composition remaining in the spent gas mixture, processing the spent gas mixture to remove unwanted components, replenishing components in the spent gas mixture in response to the concentration determination to regenerate said desired composition and recirculating resultant gaseous composition to the medical device.

The method may further comprise replenishing the components of the spent gas mixture in response to the concentration determination to generate a new desired composition Preferably, the pressure of the gaseous composition being fed to the medical device is maintained at a desired level by diverting a portion of the gaseous composition to bypass the medical device when the desired pressure is exceeded.

The spent gas may be removed and stored for later recovery in response to the concentration determination should the concentration of an active component in the mixture fall below predetermined level or an unwanted contaminant exceed a predetermined level.

Preferably, any or all of the replenishment and the removal steps can be carried out automatically in response to the concentration determination.

In a preferred embodiment, the method of the invention is incorporated into a method for the extracorporeal treatment of blood by contacting blood with a recirculating gaseous composition in a device provided with a gaseous composition.

The gaseous composition for use in the present invention preferably contains at least one high value gas, which it would be beneficial to recover after use in the process. Such gases include the noble gases, especially xenon, krypton and neon or isotopes thereof, or stable isotopes of gases such as oxygen and carbon dioxide.

In a preferred embodiment, the gaseous composition comprises xenon, preferably in an amount of at least about 10% by volume, more preferably at least about 30%, still more preferably at least about 50% and still more preferably at least about 70% by volume. Most preferably, the gaseous composition comprises xenon in an amount of about 80% by volume.

The gaseous composition preferably also comprises oxygen and more preferably consists predominantly of xenon and oxygen. Most preferably, the gaseous composition comprises xenon and oxygen in a ratio of about 80% to about 20% by volume and usually will consist solely of xenon and oxygen.

The component gases may be replenished individually or in a mixture of gases, preferably a binary mixture, of known relative proportions.

Optionally, the gaseous composition may also comprise, for example, helium or nitrogen. Helium may be provide through a further supply flow conduit from, for example, a helium cylinder or a cylinder containing a helium/oxygen mixture. Nitrogen may be provided, for example, by admitting air to the circuit. In a preferred embodiment the gas composition consists of oxygen, xenon and nitrogen. It might also include further gasses such as helium.

When oxygen is relatively quickly consumed, by a patient connected to the medical device, the oxygen concentration determining means, which may be, for example, an oxygen fuel cell sensor, preferably is connected to the first supply flow control means by a high gain electronic circuit enabling relatively rapid replenishment of oxygen to the circuit. For example, every 1% difference between the desired concentration and the detected concentration of oxygen may correspond to a flow through the oxygen (first) supply conduit of 1 liter per minute (l/min). Conversely, for means for controlling the concentration of xenon, which is relatively slowly consumed by a patient connected to the medical device, a low gain response may be more appropriate.

It is preferred that the concentration of xenon in a recirculating binary mixture with oxygen is determined with an ultrasonic gas analyser. Preferably, the ultrasonic gas analyser has an ultrahigh frequency ultrasonic transmitter, for example greater than 100 kHz.

The ultrasonic gas analyser may be used in combination with monitoring the recirculating volume to provide other information such as the concentration of contaminants in the circuit.

Similarly, comparison of the measured concentration of oxygen and xenon, in the recirculating gas, may provide information on the concentration of contaminants such as nitrogen or carbon dioxide.

When xenon or other high value gases are used, it is preferable to direct spent or recirculating gas that may from time to time be vented into a gas recovery space.

Where the high value gas is provided from a supply in a fresh gas space in a container having an ullage space, the ullage space may provide the gas recovery space.

One or more of a carbon dioxide absorber, a carbon dioxide analyser and a pressure relief device can be provided downstream from the medical device when carbon dioxide is a waste product from that device.

In a fifth aspect of the present invention, there is provided a use of a volumetric flow meter to provide feedback correction to a valve means in a flow control apparatus for controlling the flow of a gas mixture of various proportions of gaseous components, which volumetric flow meter is preferably a turbine wheel flow meter.

In a sixth aspect of the present invention, there is provided a method of providing a medical device with a gaseous composition comprising xenon and oxygen in controlled variable proportions, the method comprising:

controlling the flow of a gaseous composition of a desired composition through a conduit leading to the medical device, said conduit having a valve means located therein which valve means, when closed is subject to a gas pressure of at least a desired level. Controlling the flow of the gaseous composition is achieved by adjusting a setpoint on a potentiometer to a desired setpoint from a previous setpoint, which potentiometer is connected to a drive means for operating the valve means, said desired setpoint corresponding to a desired flow of fluid through the conduit as controlled by the valve means; generating a setpoint signal from the adjusted desired setpoint on the potentiometer; measuring the rate of flow of fluid passing through the conduit using a volumetric flow meter downstream from the valve means; generating a feedback signal from the volumetric flow meter and using said feedback signal to control the valve means.

There is also provided a use of a slowdown circuit in a setpoint signal generating means for providing a signal to a means for comparing a setpoint signal with a feedback signal provided by a parameter measuring device having an inherent response delay, which slowdown circuit compensates for the inherent response delay. Preferably, the slowdown circuit is an RC circuit.

Preferably, the RC circuit comprises a resistor in series arrangement with a potentiometer and a capacitor in parallel arrangement with the potentiometer.

The slowdown circuit described may be used in any system where a setpoint signal is subject to comparison with a feedback signal corresponding to a measured parameter, where the measurement is subject to an inherent or effective delay. Besides some volumetric flow meters, measuring devices whose measurement is subject to such delay by, for example, a slow response time, include thermocouples (for example, for use in gas turbine engines), and other gas analysis devices.

In general, it would be highly convenient if the rate of flow of gas could be controlled independently from more than one location, particularly so when controlling the flow of gas to one or more medical devices, so that, for example, both an anaesthetist and a clinician may conveniently alter the flow rate. This is particularly advantageous where gas is circulating through a main circuit for delivery to either a cardiopulmonary bypass oxygenator or a ventilator, in which the same gas source may be used by both an anaesthetist operating a ventilator and a clinician operating a cardiopulmonary bypass oxygenator.

Accordingly, in another aspect of the present invention, there is provided an apparatus for controlling the rate of flow of gas through a conduit, said apparatus comprising a flow regulator for regulating the rate of flow of gas through a conduit, a digital potentiometer for providing a controllable output signal for controlling the flow regulator to provide a selected flow rate of gas, a first digital encoder, which is a rotary encoder, having an output for selectively increasing and decreasing the resistance of the potentiometer, and at least one other digital encoder having an output for selectively increasing and decreasing the resistance of the potentiometer, the arrangement being such that the voltage of the output signal from the digital potentiometer can be selectively increased and decreased by independent manipulation of the first digital encoder and the at least one other digital encoder thereby enabling independent control of the rate of flow of gas through the conduit from more than one location.

Preferably, there is at least one other rotary encoder and ideally, for example, in use with the embodiment where the flow of gas to be regulated is to one of two medical devices, e.g. a cardiopulmonary bypass oxygenator and an artificial ventilator, there are two rotary encoders. There may, however, be any number of rotary encoders, as necessary or convenient.

Preferably, there is an isolating device connected to the outputs of each digital encoder. Where the digital potentiometer comprises an increment input for receiving signals from a first output of each of the digital encoders, and an up input and a down input for receiving signals from a second output of each of the digital encoders, it is preferred that the apparatus comprise isolating devices connected to each of the first and second outputs of the digital encoders. The isolating device may be any suitable device for preventing the circuit that connects at least two digital encoders to the same input of the digital potentiometer from shorting. Most preferably, the isolating device is an isolating capacitor, which is preferably in a parallel arrangement with a resistor.

The up input and down input of each digital potentiometer are preferably in the form of a single U/Dbar input.

Preferably, a first isolating device is connected to the first outputs of the digital encoders and a second isolating device is connected to the second outputs of the digital encoders.

Typically, the first and second outputs of the digital encoders produce pulsed signals which are 90° out of phase. Where the digital encoder is a rotary encoder, it is preferable that the first output leads the second output when the switch on the rotary encoder is rotated in a clockwise direction. Preferably, such an arrangement will allow the voltage of the output of the digital potentiometer to be increased by clockwise rotation the switch on the rotary encoders.

It is preferred that the provision of dual control of the rate of flow of gas is achieved by having at least two rotary encoders connected to a digital potentiometer by simple, passive electronic components.

The following is a description by way of example only and with reference to the accompanying drawings of presently preferred embodiments of the invention. In the drawings:—

Figure 1:
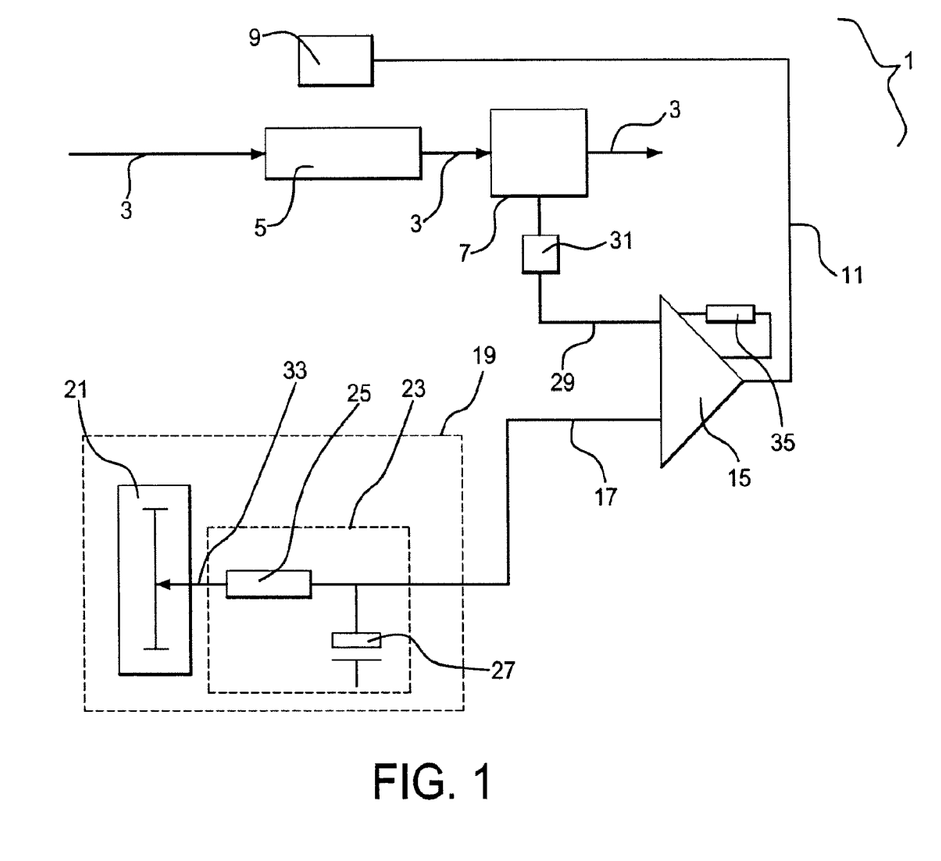
FIG. 1 is a circuit diagram of an example of a volume flow controller apparatus in accordance with an example of an embodiment of one aspect of the present invention.

With reference to FIG. 1, the volume flow controller (generally designated 1) for controlling the flow of a gas or a gas mixture comprises a gas flow conduit 3 which directs a flow of gas through a regulator e.g. a solenoid valve 5, for regulating the gas flow, and through a turbine wheel flow meter 7, for measuring the volume of gas passing through the valve 5. Valve 5 is driven by driver 9 in response to an adjustment signal 11 from an amplifier 15.

The valve 5 functions as a means to regulate the flow of gas. The driver 9 functions as a means to drive the valve 5. The turbine wheel flow meter is an example of a volumetric flow meter. Further examples of flow meters that are volumetric flow meters are described below. The amplifier 15 functions as a comparator for generating the adjustment signal The adjustment signal 11 of amplifier 15 is composed of two input signals. One input signal (the positive input) is the setpoint signal 17 produced by a setpoint signal generator which functions as setpoint generating means 19. In this example, the setpoint generator comprises a potentiometer 21 variable between 0V and 5V corresponding to a desired gas flow rate of from 0 l/min to 10 l/min, the desired setpoint, and 'slowdown' circuit 23 which has a 330 kΩ resistor 25 and a 40 µF capacitor 27. Slowdown circuit 23 causes the setpoint signal, for the positive input to amplifier 15, to change slowly over time from a value corresponding to the starting (or previous) setpoint to a value corresponding to the desired setpoint.

The time over which the change takes place is a function of the resistance of resistor 25, the capacitance of capacitor 27 and the difference between the desired setpoint voltage and the previous setpoint voltage. The other input signal for the amplifier 15 (the negative input) is feedback signal 29, which is the output signal of turbine wheel flow meter 7 after treatment by a frequency to voltage converter circuit 31, which gives an output of 0V to 5V with from 0 l/min to 10 l/min applied to flow meter 7 in a largely linearly proportional relationship. The response time of flow meter 7 to changes in the flow of gas through valve 5 is up to 8 seconds, depending upon the magnitude of the change.

In use, the operator (e.g. a clinician) sets potentiometer 21 to the desired gas flow rate. The potentiometer output signal 33 is fed to slowdown circuit 23 and the generated setpoint signal 17 is input to operational amplifier 15. The amplifier 15 subtracts the feedback signal 29 (initially zero) from the setpoint signal 17, which difference is subject to a 20× gain, due to resistor circuit 35, and provides adjustment signal 11. The amplifier output signal 11 is input into driver 9, which correspondingly adjusts solenoid valve 5, which is initially subject to a gas pressure of 100 mbarg (110 kPa).

The rate of the resultant gas flow is measured by turbine wheel flow meter 7, which typically takes 6 or 7 seconds to provide an accurate measurement of the gas flow rate, due to the delay in the turbine wheel increasing or decreasing its rate of rotation. The signal from the flow meter 7 is converted by converter circuit 31 and the resulting feedback signal 29 is fed to amplifier 15, where it is compared with setpoint signal 17 corresponding to the desired value on potentiometer 21, subject to a delay by slowdown circuit 23 to compensate for the delay in response by the turbine wheel flow meter 7. The resulting output signal 11 from the amplifier of signal generating means 13 includes a correction factor from feedback signal 29. Accordingly, if the desired flow rate remains unchanged, the feedback signal will provide a correction signal as output signal 11 to adjust solenoid valve 5 so that a flow of gas corresponds more correctly to the desired flow of gas.

The turbine wheel flow meter 7 is an example of a truly volumetric flow meter. Other examples include a positive displacement meter, a vortex shedding meter, a correlation flow meter or a near-positive displacement meter such as a swirl plate turbine meter. These and other volumetric flow meters are described in "Industrial Gases" by Neil A. Downie, published by Blackie Academic publishers (an imprint of Chapman & Hall), 1997, ISBN 0751403520, the entire contents of which are incorporated herein by reference.

All these truly volumetric meters measure gas volume. When such a meter has measured one liter of gas per minute, it will indicate the same, or very nearly the same, whether that gas happens to be a light gas like hydrogen or a heavy gas like sulphur hexafloride. In other words, a true measure of the volume of the gas flow is obtained irrespective of the composition of the gas flow.

This contrasts with gas flow sensors such as thermal mass flow meters, which measure the convective transfer of heat by flowing gas. These meters indicate a flow dependent upon the composition of the gas. In the case of a venturi or orifice meter, for example, hydrogen will indicate almost ten times less than sulphur hexifloride at the same volumetric volumetric flow rate. In the case of a thermal mass flow meter, sulphur hexafloride will give a reading just three and half times that expected for hydrogen or air at the same volumetric flow rate.

In the present system, a truly volumetric flow meter i.e. a flow meter the results from which are not dependent on composition of gas in the flow, is used.

Positive displacement meters rely on the fact that the gas is at a known pressure, and pushing the gas (gently, so that the known pressure is not changed) through a cylinder/piston or similar positive displacement device of known volume enables flow to be measured. Vanes, gears, pistons or diaphragms may be used to separate the fluid. These separate the gas into known volumes such that the number of these known volumes can be counted over time to provide an indication of the true volumetric flow.

A turbine meter typically consists of a rotor, often somewhat like a high-pitch marine propeller in form, rotating on an axis down the middle of a pipe section. The rotor may simply operate a meter display via reduction gears, or alternatively the rotor may contain a magnet to give electrical pulses as it passes a pick-up coil mounted on the pipe section wall.

The swirl plate turbine meter is a particularly simple form of turbine meter. It comprises a fixed stator which imparts a rotation to the gas. This rotation is then sensed by a thin flat vane rotating about a central axis. The low inertia of the vane relative to a standard turbine impeller means that the swirl plate turbine responds more quickly to changes in flow rate.

In a vortex shedding meter, an unstreamlined body is placed in a gas stream. As the gas flows in the stream, it generates a regular series (a "von Karman street") of eddies i.e. vortices which are carried along with the stream behind the body. Provided the stream velocity lies between certain limits, the number of eddies is precisely proportional to the volume of gas that has passed. The eddies are normally detected with a small piezoelectric microphone or with small anemometer hot wire sensors.

Correlation flow meters rely on turbulence in the flow of gas in a pipeline. A gas parameter, such as instantaneous pressure P(t), is measured at two points x and y along a gas conduit i.e. a pipeline, and the signals at the two points, one upstream of the other by a short distance, are correlated. A correlation sum $\Sigma P_x(t+\Delta T)P_y(t)$ is determined based on the value of P(t) for a number of values of t. $\Delta T$ represents a selected offset time. The sum is repeated for different values of $\Delta T$ and a maximum value of the correlation sum is determined. This occurs when $\Delta T$ is such that the two signals $P_x$ and $P_y$ have a similar time sequence. Based on a knowledge of the pipeline flow characteristics, the distance from x to y and the pipeline cross section an estimate for volume flow can be calculated.

Figure 2:
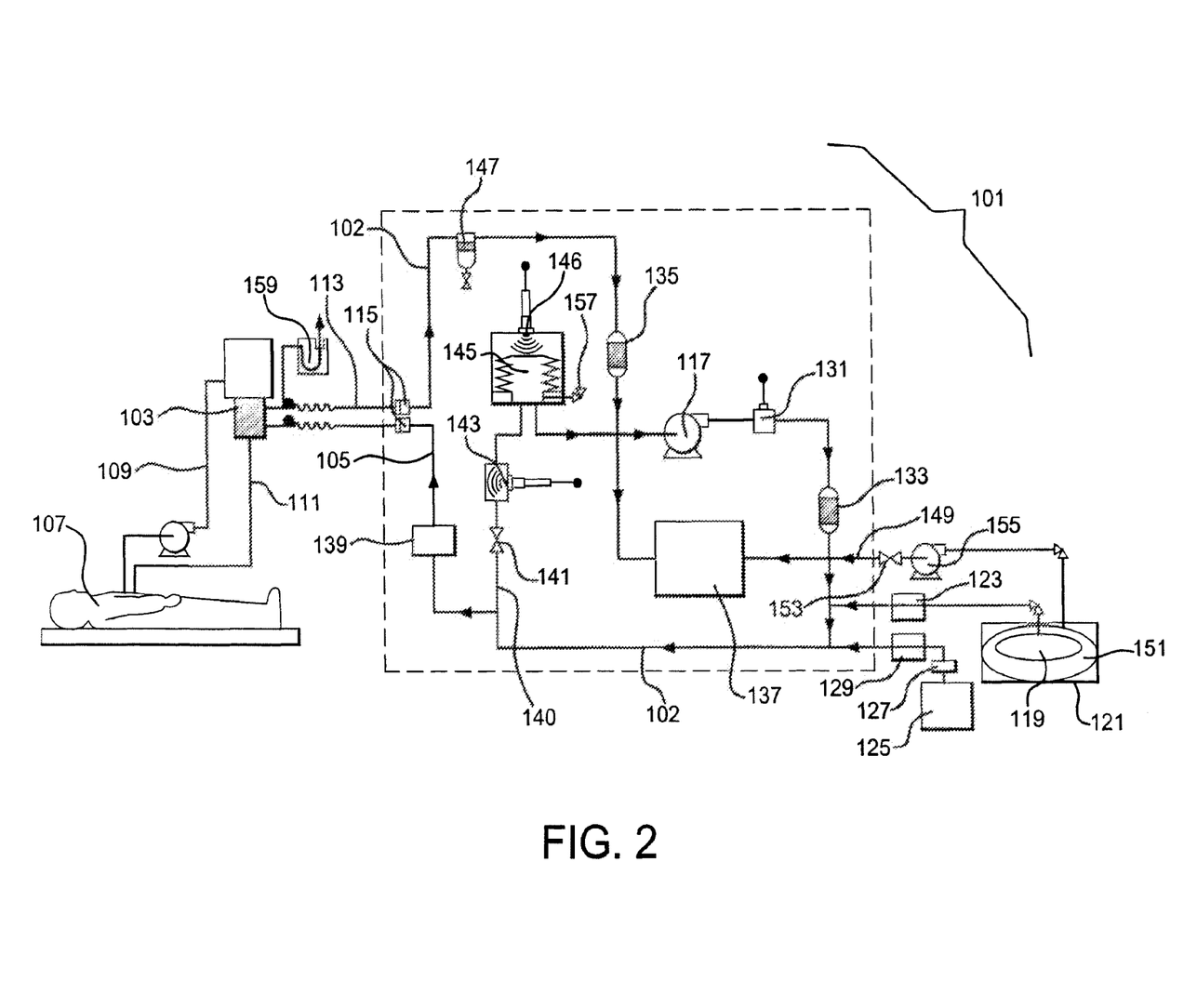
FIG. 2 is a diagrammatic representation of the use of the volume flow controller of FIG. 1 in a gas recirculation system for providing gas to a cardiopulmonary bypass oxygenator.

With reference to FIG. 2, which depicts a volume flow controller 139 of the type in FIG. 1 incorporated into a gas recirculation system for providing gas to a cardiopulmonary bypass oxygenator, a xenon/oxygen mixture in a ratio of 80% xenon to 20% oxygen is fed into the main circuit 102 of the apparatus (generally designated 101) from a xenon/oxygen supply in fresh gas space 119 of container 121 via xenon mass flow controller (MFC) 123.

The oxygen content of main circuit 102 may be topped up from oxygen cylinder 125 via regulator 127 and oxygen mass flow controller (MFC) 129.

One or more (preferably four) diaphragm pumps 117 pump the xenon/oxygen mixture around the circuit 102 at a rate of up to 20 liters per minute (l/min) at a pressure of up to 150 millibar gauge (1150 kPa).

The gaseous composition is fed to cardiopulmonary bypass (CPB) oxygenator 103 via gas outlet 105, which is regulated by volume flow controller 139, which may be set at a desired level by the operator. The potentiometer 21 (see FIG. 1) of volume flow controller 139 is set using a dual control potentiometer circuit (see FIG. 5) whereby two rotary encoders are connected to a digital potentiometer to enable the volume flow control to be set at a desired level from two different locations, for example by a clinician or by an anaesthetist. This dual control potentiometer circuit is of the kind described below with reference to FIG. 5.

CPB oxygenator 103, which is typically a membrane oxygenator, is fed unoxygenated blood from a patient 107 via unoxygenated blood conduit 109 and returned to the patient 107 via oxygenated blood conduit 111. Spent gas from the CPB oxygenator 103 is fed through gas inlet 113 and then through water trap 147, primary carbon dioxide absorber 135 and pump(s) 117.

Gas passing through the inlet 113 and outlet 105 pass through respective bacterial filters 115 to protect the patient 107 from contamination from the apparatus 101 and vice versa.

In order to ensure that a constant flow of gas at the set pressure is supplied to the oxygenator 103 and thus available to the patient's blood, excess gas is fed through bypass conduit 140 via pressure maintaining valve 141 upstream from the volume flow controller 139. Pressure maintaining valve 141 is a valve which allows gas flow through the bypass conduit 140 only when the pressure exceeds a predetermined level, for example 30 mbarg (103 kPa).

Downstream from the pressure maintaining valve 141, the gaseous composition is analysed for xenon content using ultrasonic xenon analyser 143. The gas is then fed via bellows 145, which expand to take up any additional volume of gas in the apparatus or contract to compensate for loss of volume in the apparatus, and rejoins the main circuit 102 upstream of pump(s) 117.

The oxygen concentration in the main circuit 102 is monitored by oxygen fuel cell sensor 131 situated in the main circuit 102 downstream from pump(s) 117. The gas is then fed through backup carbon dioxide absorber 133, which removes residual carbon dioxide from the recirculating gas. The carbon dioxide removed by absorbers 133 and 135 has entered via the oxygenator 103 after being flushed from the patient's blood. At least absorber 135 should be replaced with each use of the system.

Downstream from the backup carbon dioxide absorber 135, a small sample of gas is drawn from the main circuit and fed to analyser unit 137 to be analysed for carbon dioxide, via an infra red gas analyser, to ensure that the carbon dioxide absorbers are working efficiently and for oxygen, via a paramagnetic gas analyser, as a backup to the oxygen fuel cell sensor 131. The sample is returned to the main circuit upstream from the pump(s) 117.

Recovery gas conduit 149 feeds spent gas from the main circuit 102 at a point downstream from the backup carbon dioxide absorber 135 to the ullage space 151 of container 121, via recovery valve 153 and compressor 155.

An atmospheric vent 157 from bellows 145 enables the gas within the apparatus to be vented to atmosphere if desired.

There is a U-tube relief device 159 on the gas inlet 113 to protect the oxygenator 103 and patient 107 in the event of any back pressure from the apparatus 101.

Addition of fresh gas to the apparatus is controlled by an analog electronic circuit (not shown) between oxygen fuel cell sensor 131 and oxygen MFC 129 for fresh oxygen addition and by an analog electronic circuit between an ultrasonic level sensor 146 measuring the position of the bellows and the xenon MFC 123 for fresh xenon/oxygen mixture addition.

As well as monitoring the concentration of oxygen in the main circuit 102, oxygen fuel cell sensor 131 enables the oxygen concentration to be controlled. The operator may choose a set point on the sensor 131 corresponding to the desired oxygen concentration. If oxygen concentration measured by sensor 131 falls below the set point, oxygen MFC 129 is triggered to feed fresh oxygen into the main circuit 102 at a rate proportional to the difference between the oxygen level set point and the oxygen sensor 131 measurement via the high gain circuit connecting oxygen MFC 129 to sensor 131.

Typically, the high gain oxygen control circuit (not shown) will have a gain of 1, corresponding to an oxygen flow rate through oxygen MFC 129 and into the main circuit 102 of 1 l/min for every 1% difference between the oxygen set point and the measured oxygen level.

The xenon concentration of the main circuit is controlled by ultrasonic bellows level sensor 146. The operator may set the desired level on a potentiometer (not shown) which is connected to sensor 146, which corresponds to an expanded level of the bellows 145. This level corresponds to the volume in the system and, given that the oxygen concentration is known, to a desired concentration of xenon. When the sensor 146 detects that the bellows 145 has fallen below the desired level, xenon MFC 123 is triggered to feed fresh oxygen/xenon mixture into the main circuit 102 at a rate proportional to the difference between the potentiometer set point and the level measured by bellows sensor 146, via the low gain circuit (not shown) connecting sensor 146 to xenon MFC 123.

Typically, the xenon low gain circuit will have a gain of 0.1, corresponding to a flow of fresh xenon/oxygen mixture into the main circuit 102 of 0.1 l/min for every 1% difference between the potentiometer setpoint and the level measured by bellows sensor 146.

The various sensor readings and flow rates are displayed on a monitoring unit (not shown).

In use, oxygen is consumed and replaced by carbon dioxide via the CPB oxygenator 103. The operator may select the flow rate to the oxygenator 103 by using volume flow controller 139. This effectively controls the rate that carbon dioxide is flushed from patient's blood into the apparatus and hence provides some control as to the relative acidity or alkalinity of the patient 107.

Carbon dioxide is absorbed by primary carbon dioxide absorber 135 and the reduction in the oxygen level is detected by fuel cell sensor 131 triggering, via the high gain circuit, replenishment of oxygen levels under the control of oxygen MFC 129.

Xenon sensor 143 measures the xenon concentration in the main circuit 102. This reading may be compared to other readings to reach various conclusions. For example, if the oxygen concentration measured by oxygen fuel cell sensor 131 does not equal 100 minus the xenon concentration measured by xenon sensor 143, it is indicative of contamination, for example by carbon dioxide or nitrogen, and the operator may be alerted to vent the apparatus to atmosphere or recover the used gas. Alternatively, this may be done automatically at a preset level. The xenon sensor 143 is also used to monitor the xenon concentration predicted from the level of the bellows. Similarly, if these two readings do not agree, this may be indicative of too much carbon dioxide, nitrogen or oxygen. As a result, the operator may again choose to vent to atmosphere or recover the used gas.

If the gas volume in the apparatus is increased, the level of bellows 145 increases. If the level of bellows 145 exceeds a preset level, gas is vented from the apparatus, again either manually or automatically, via atmospheric vent 157 and/or xenon recovery valve 153. Optionally, the sensor 146 may be connected to ultrasonic analyser 143 so that when the bellows 145 upper level is exceeded, vent 157 or valve 153 is selectively opened depending on the xenon content of the gas measured by analyser 143.

It will be appreciated that when a patient is on a respiratory support system such as an artificial lung, ventilator or anaesthetic machine, they must be provided with sufficient fresh oxygen for their blood to keep the haemoglobin nearly saturated and they must also have carbon dioxide ($CO_2$) washed out of their blood to a controlled low level.

The total flow of gas to a patient under anaesthetic or connected to an oxygenater system (artificial lung) must be controlled to control the wash out of $CO_2$. The larger the total gas flow, the greater the rate at which $CO_2$ will be washed out of the patient and consequently larger total gas flows enable lower concentrations of $CO_2$ to be achieved in the patient's blood. In the case of a once-through gas system, i.e. a system in which gas is substantially not recirculated, the fresh gas flows e.g. oxygen flow, air flow etc. can simply be added up arithmetically to give a total gas flow. This total gas flow can be controlled to control the $CO_2$ wash out. The gas flow can be controlled, for example, by increasing or decreasing the input of one or more of the components of the gas flow e.g. oxygen, to the system.

In the case of a closed circuit system or a partially closed-circuit system the fresh gas flows do not add up to the total flow for the purposes of calculating $CO_2$ wash out. Indeed, as shown above, the recirculating flow into the patient's blood is sensed and controlled. In an example of an embodiment of the present invention, in the case of a patient gas system in which the gas composition varies greatly, a flow controller is used which controls true volumetric flow.

Oxygen concentration and flow control can be achieved in a closed-circuit system by controlling the oxygen concentration in the recirculating gas, and then controlling the recirculation flow. The product of $O_2$ concentration and total recirculated flow indicates the $O_2$ flow into the patient. Measuring the $O_2$ concentration coming out of the patient and multiplying this by the recirculated flow gives the $O_2$ flow out of the patient and in this way $O_2$ uptake can be estimated.

In an example of an embodiment of the present system it is desirable to use a mixture of xenon and oxygen as a gas mixture in a gas recirculating flow controller. However, as explained above, the addition of xenon and any change in the proportion of xenon in the gas mixture will cause the set-point of the flow controller to change unless that flow controller employs a true volumetric sensor or flow meter. The proportion of xenon might be changed because, for example, the anaesthetist wants to give the patient a higher proportion of oxygen. The use of a truly volumetric flow meter allows an anaesthetist to set a recirculation flow rate in order to achieve a satisfactory $CO_2$ wash out from a patient. Importantly, the flow rate will not change even if there is variation in the relative proportions of xenon and oxygen in the gas flow. This is because the parameters of the gases xenon and oxygen which might have an effect on the reading from a flow sensor such as a mass flow sensor will have no effect on the reading obtained from a truly volumetric flow meter.

Figure 3:
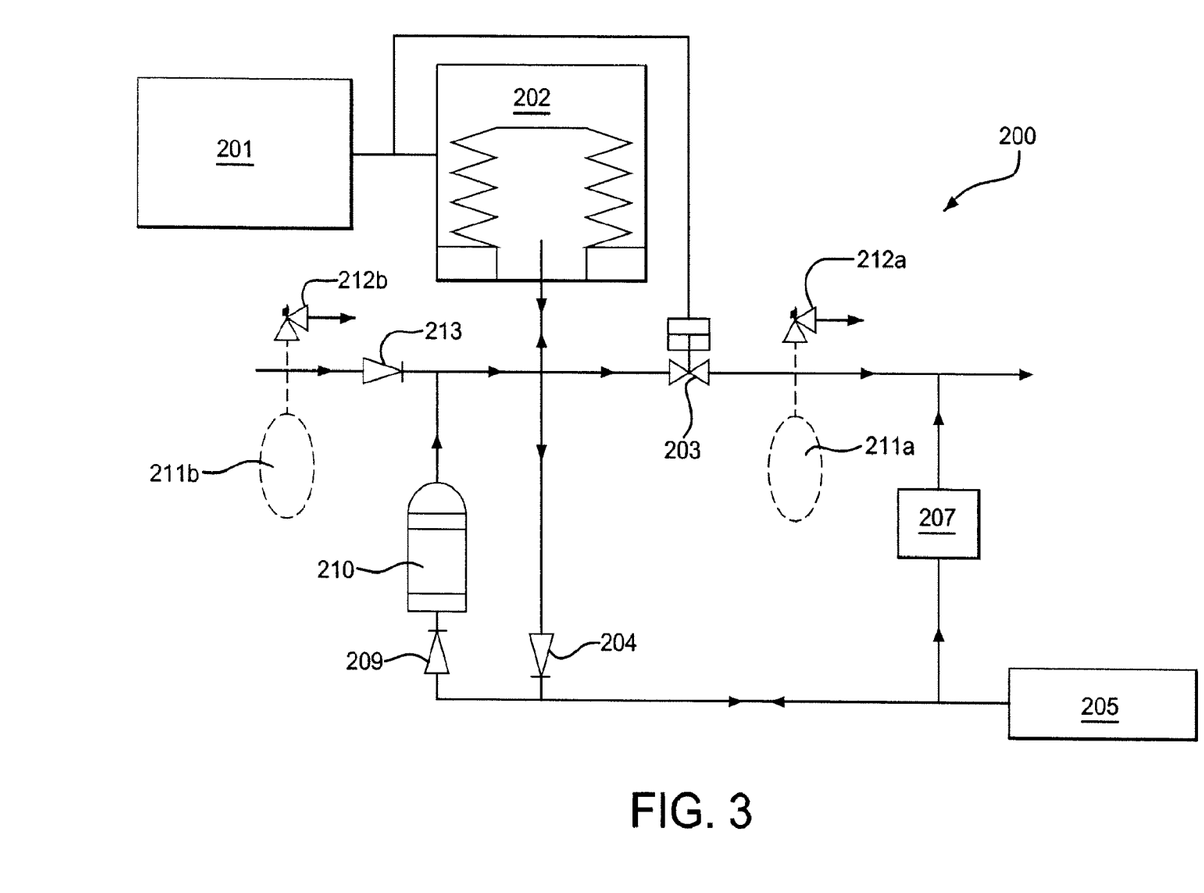
FIG. 3 is a diagrammatic representation of an example of a ventilator circuit for introduction into the apparatus of FIG. 2 to replace the cardiopulmonary bypass oxygenator.

Referring now to FIG. 3, a ventilator circuit generally designated 200 is connected at the filters 115 of the apparatus of FIG. 2 to replace the CPB circuit. Fresh gas passes through the outlet filter 115 (see FIG. 1) into the ventilator circuit 200 via a check valve 213 to provide gas to the ventilator thereby maintaining the oxygen and xenon concentrations in the ventilator circuit 200 at the required levels.

The ventilator circuit 200 includes a conventional ventilator 201 of the kind providing a positive drive gas pressure (above atmospheric pressure) in pulses for a second or two, followed by a slightly longer period at atmospheric pressure. The period, cycle time and power of the drive gas pressure is set, in conventional manner, to match the needs of the patient 205.

When the ventilator drive pressure is positive, it pushes gas out of the bellows of a bellows assembly 202 via a control valve 203 and a check valve 204 into the lungs of the patient 205. Valve 203 is a pneumatically operated valve that is held closed by the positive ventilator drive pressure during the inflation of the patient's lungs. When the ventilator 201 proceeds to the atmospheric pressure part of its cycle, which allows the patient's lung to relax and deflate, exhaled gas (oxygen removed, carbon dioxide added) flows from the lungs via a check valve 209 to a soda-lime absorber canister 210. The canister 210 absorbs carbon dioxide from the exhaled gas and then allows it to flow back to refill the bellows of the bellows assembly 202. This gas may then be pumped back to the patient's lungs by the bellows during the next positive pressure pulse from the ventilator 201. The level of carbon dioxide in the gas from the patient's lungs is measured continuously by a $CO_2$ analyser 207, which monitors both the end-tidal (peak) $CO_2$ level, which gives an indication of the patient's correct respiration, and the minimum $CO_2$ level, which gives an indication of exhaustion of the soda-lime 210.

When the ventilator 201 is in the atmospheric pressure part of its cycle, the valve 203 is open and, if the bellows inside the bellows assembly 202 has reached the top of its travel and the gas pressure becomes positive enough (a few millibar), gas may flow from the bellows into an optional bag 211a, past an optional pressure relief valve 212a and back to the gas recycling circuit 102 (see FIG. 1) via an outlet 208 and filter 115 (see FIG. 1). The bag 211a and optional pressure relief valve 212a are needed if the tubing connecting the recycling circuit 102 to the ventilator circuit 200 are not large enough to assure correct operation of the bellows pressure relief via valve 203. In an alternative arrangement, the bag 211b and relief valve 212b are located upstream of the check valve 203.

Figure 4:
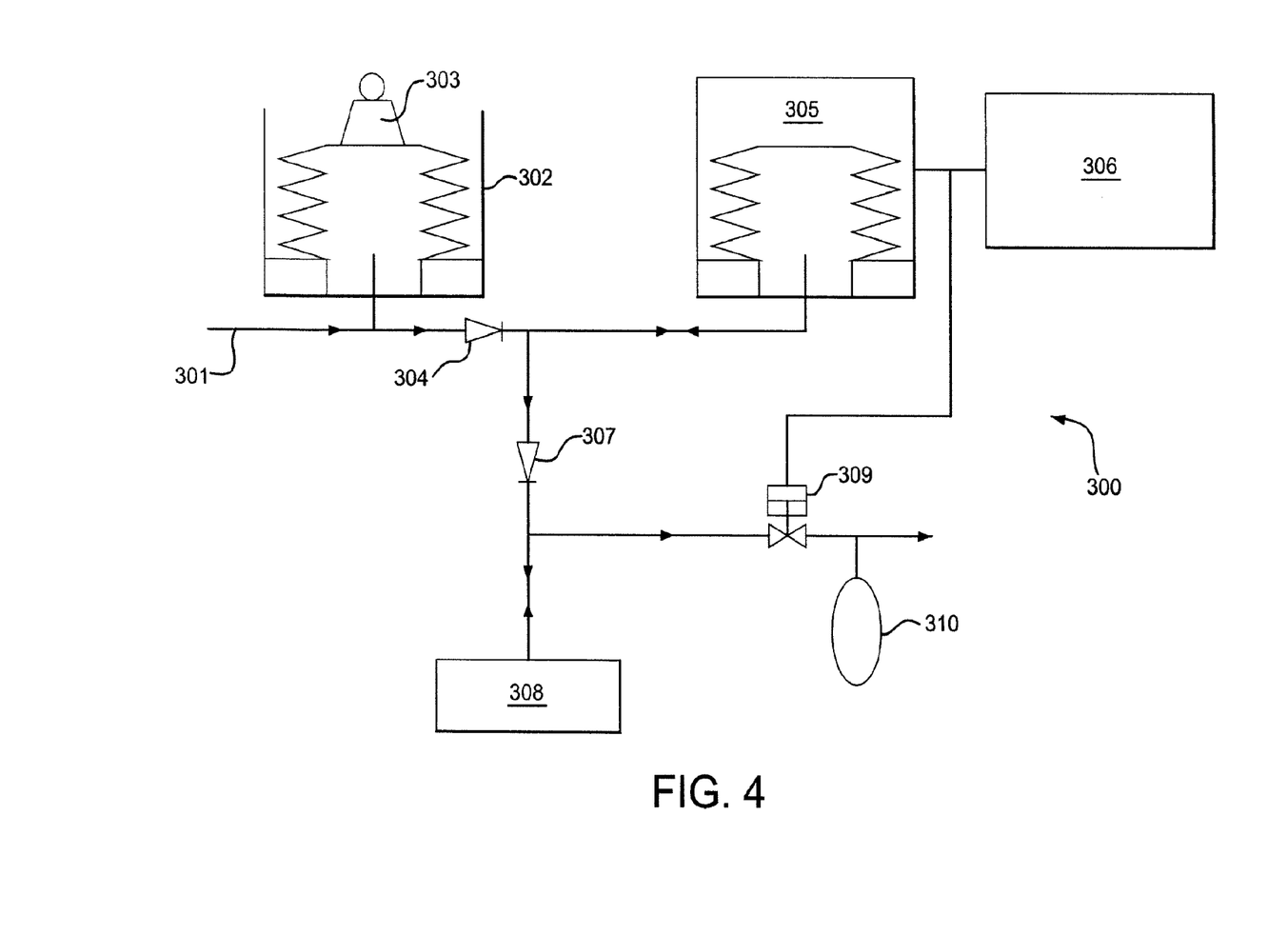
FIG. 4 is a diagrammatic representation of another ventilator circuit for introduction into the apparatus of FIG. 2 to replace the cardiopulmonary bypass oxygenator.

FIG. 4 shows an alternative ventilator circuit 300 for connection to gas recycling circuit 102 of FIG. 1 in corresponding manner to the ventilator circuit 200 of FIG. 3. It is specially designed to ensure that the patient 305 receives fresh gas from the recycling circuit 102 of FIG. 2 and that the exhaled gas is not mixed with fresh gas but is fed back to the recycling circuit 102.

Fresh gas from the outlet filter 115 (see FIG. 2) is fed to the ventilator circuit 300 at inlet 301. An optional feed bellows assembly 302 is connected downstream of the inlet and has a weight 303 to ensure that it runs at a small positive pressure, which is sufficient to feed gas through a check valve 304 to raise the bellows in a ventilator bellows assembly 305 when the drive gas pressure from ventilator 306 is atmospheric.

The ventilator 306 and bellows assembly 305 function in a similar way to that normally employed in prior art ventilator systems. Periodically, ventilator 306 applies positive (above atmospheric) gas pressure to the outside of the bellows in the bellows assembly 305, collapsing the bellows and forcing gas from inside the bellows through a check valve 307 to the lungs of the patient 308. The ventilator drive gas to the bellows is also applied to a pneumatically operated valve 309 to close it, so that all the gas from the bellows assembly 305 goes to the patient 308.

When the gas pressure from the ventilator 306 is relaxed back to atmospheric pressure, the bellows in bellows assembly 305 re-inflates with fresh gas from the inlet 301 and the feed bellows 302. The check valve 307 is biased with a spring or weight so that it only opens at a few millibar, assuring that 100% of fresh gas flows into the bellows assembly 305.

Simultaneously with the refill of the main bellows assembly 305 the patient's lungs relax, exhaling gas containing less oxygen and more carbon dioxide relative to fresh gas. The exhaled gas flows through pneumatically operated valve 309, which is now open to the gas return circuit (since the drive gas pressure is atmospheric). The gas return circuit may optionally include a variable gas volume comprising an additional bellows or flexible bag 310.

Figure 5:
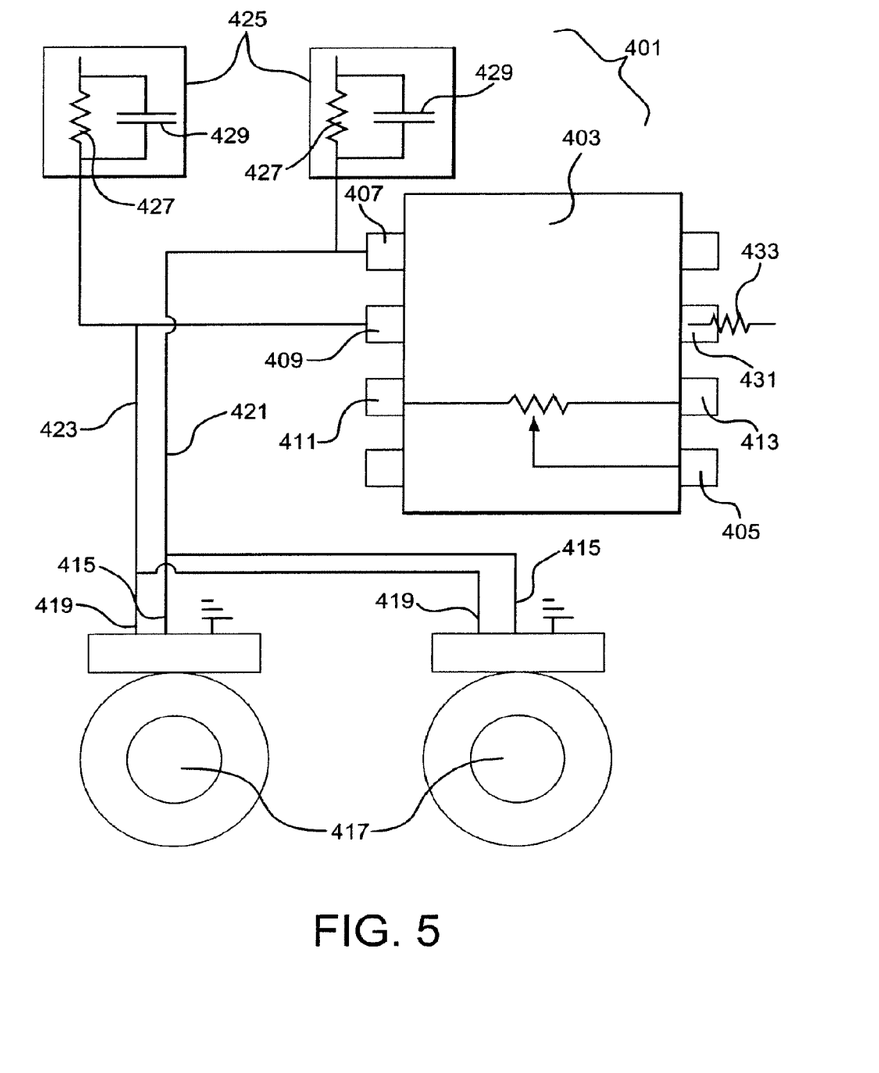
FIG. 5 is a circuit diagram of an example of a dual control device for use in accordance with an aspect of the present invention.

With reference to FIG. 5, a dual control device (generally designated 401) for controlling the output signal of a digital potentiometer comprises an 8-pin 100 $k\Omega$ digital potentiometer 403 having an output port 405, an increment input port 407, and a U/Dbar input port 409. A voltage of 5V is applied between the H-pin 411 and the L-pin 413 corresponding to the range (0-5 V) of signal from the output port 405.

The first outputs 415 (or "B-switch") of two digital rotary encoders 417 are connected to the increment input port 407 of the digital potentiometer 403, to constitute incremental input circuit 421.

The second outputs 419 (or "A-switch") of the rotary encoders 417 are connected to the U/Dbar port 409 of the digital potentiometer 403, and constitute U/Dbar input circuit 423.

Rotary encoders 417 are electronic control knob devices which produce pulses as the knob is rotated. The two outputs 415, 419 of the rotary encoders 417 are each connected momentarily with a "terminal C" which is grounded, during rotation of the knob.

Isolating devices 425 are connected to each of the incremental input circuit 421 and the U/Dbar input circuit 423 in parallel with the rotary encoders 417. The isolating devices 425 each comprise a 12 $k\Omega$ pull-up resistor 427 and a 10 $\mu F$ isolating capacitor 429, connected in parallel. These isolating devices 425 also facilitate "debouncing", by which the connections made by the rotary encoder 417 with the first and second outputs on rotation of the switch are stabilised. Debouncing is desirable because mechanical vibration of the encoder contacts at, for example, the encoder outputs 415, 419, can result in multiple increments being sent to the digital potentiometer inputs 407, 409. CS-pin 431 has a 12 $k\Omega$ pull-down resistor 433 connected to it.

By clockwise rotation of the switch on either of the rotary encoders 417, the voltage at the output 405 of the digital potentiometer 403 is increased incrementally. Similarly, by anticlockwise rotation of the switch on either of the rotary encoders 417, the voltage at the output 405 of the digital potentiometer 403 is decreased incrementally.

If both rotary encoders 417 are operated simultaneously, then advantageously the digital potentiometer 403 will "freeze" in position until only one of the rotary encoders 417 is being operated, when that rotary encoder will again control the digital potentiometer 403. This is very useful in that it prevents conflicting signals being sent to the digital potentiometer 403 by the rotary encoders 417

During open heart surgery, both the anaesthetist and the perfusionist can control certain parameters, especially oxygen concentration and gas flow rate of gas mixture to a cardiopulmonary bypass oxygenator, by manipulation of the two rotary encoders 417 connected to digital potentiometer 403 which controls the parameters in the gas delivery system. This dual control is important because although the anaesthetist must have control of gas to the patient during switch over from ventilator to oxygenator and vice versa, and must retain overall control of patient gas, the perfusionist takes over responsibility for the correct perfusion of oxygen into the patient's blood while the patient's heart is bypassed and the blood being pumped to the cardiopulmonary oxgyenator.

Embodiments of the present invention have been described with particular reference to the examples illustrated. However, it will be appreciated that variations and modifications may be made to the examples described within the scope of the present invention.

The invention claimed is:
1. Apparatus comprising:
 a medical device requiring a supply of a gaseous composition comprising a first gas and a second gas;
 a main circuit for recirculating gas through the medical device and comprising:
  a circulation pump for pumping gas through the main circuit,
  a gas outlet connected to the medical device,
  a gas inlet connected to the medical device, a first supply conduit for supply of gas of a first composition to the main circuit, a second supply conduit for supply of gas of a second composition different from said first composition to the main circuit, a gas outlet flow controller for controlling the flow of gas to the medical device;

a first supply flow controller for controlling the flow of gas through the first supply conduit; and a second supply flow controller for controlling the flow of gas through the second supply conduit;

a concentration determiner for determining the concentration of at least one gas of the gaseous composition within the main circuit; and a vent for venting gas from the main circuit, wherein at least one of the gas outlet flow controller, the first supply flow controller and the second supply flow controller comprises a regulator, a setpoint signal generator and a volumetric feedback correction system, the volumetric feedback correction system including a volumetric flow meter for determining a volumetric rate of flow of gas independently of the composition of the flow of gas.

2. The apparatus according to claim 1, which further comprises:

a first circuit gas concentration controller, including the first supply flow controller, for controlling the concentration of the first gas in the gaseous composition, which first circuit gas concentration controller comprises a first gas concentration determiner for determining the concentration of the first gas in the gaseous composition and communicating with the first supply flow controller for controlling flow of the first gas through the first supply conduit; and a second circuit gas concentration controller, including the second supply flow controller, for controlling the concentration of the second gas in the gaseous composition, which second circuit gas concentration controller comprises a second gas concentration determiner for determining the concentration of the second gas in the gaseous composition and communicating with the second supply flow controller for controlling flow of the second gas through the second supply conduit, whereby on reaching a respective predetermined level, each of said determiners triggers the corresponding flow controller to increase the flow of the corresponding gas to the circuit.

3. The apparatus according to claim 2, wherein the first circuit gas concentration controller comprises a first gas concentration determiner for determining the concentration of the first gas in the gaseous composition and communicating with the first supply flow controller for controlling flow of the first gas through the first supply conduit and the second circuit gas concentration controller comprises a monitor for monitoring the relative increases and decreases in gas volume in the circuit and communicating with the second supply flow controller for controlling flow of the second gas through the second supply conduit, whereby on reaching a respective predetermined level, each of said determiner and said monitor triggers the corresponding flow controller to increase the flow of the corresponding gas to the circuit.

4. The apparatus according to claim 2, wherein the first circuit gas concentration controller comprises a relatively high gain analog electrical circuit and the second circuit gas concentration controller comprises a relatively low gain analog electrical circuit, whereby the increase in flow rate of the first gas is relatively quick and the increase in flow rate of the second gas is relatively slow.

5. The apparatus according to claim 3, wherein the first circuit gas concentration controller comprises a relatively high gain analog electrical circuit and the second circuit gas concentration controller comprises a relatively low gain analog electrical circuit, whereby the increase in flow rate of the first gas is relatively quick and the increase in flow rate of the second gas is relatively slow.

6. The apparatus according to claim 1, which further comprises an ultrasonic xenon analyser.

7. The apparatus according to claim 1, wherein the medical device is selected from a cardiopulmonary bypass oxygenator and an artificial ventilator.

8. The apparatus according to claim 7, wherein the medical device is a cardiopulmonary bypass oxygenator.

9. The apparatus according to claim 8, which apparatus further comprises one or more of a carbon dioxide absorber, a carbon dioxide analyser and a pressure relief device downstream from the oxygenator.

\* \* \* \* \*